United States Patent [19]
Schultz et al.

[11] Patent Number: 5,456,720
[45] Date of Patent: Oct. 10, 1995

[54] PROSTHESIS FOR REPAIR OF DIRECT SPACE AND INDIRECT SPACE INGUINAL HERNIAS

[76] Inventors: Leonard S. Schultz, 8883 Flesher Cir., Eden Prairie, Minn. 55347; Joseph J. Pietrafitta, 5571 Bristol La., Minnetonka, Minn. 55343; John N. Graber, 5039 Bryant Ave. S., Minneapolis, Minn. 55409; David F. Hickok, 2300 Oliver Ave. S., Minneapolis, Minn. 55405

[21] Appl. No.: 126,166

[22] Filed: Sep. 23, 1993

Related U.S. Application Data

[63] Continuation of Ser. No. 653,083, Feb. 8, 1991, abandoned.
[51] Int. Cl.⁶ ........................................................ A61F 2/04
[52] U.S. Cl. ................................. 623/12; 600/37; 606/213
[58] Field of Search ................................. 623/12; 600/37; 602/60; 606/213, 151; 383/84

[56] References Cited

U.S. PATENT DOCUMENTS 2,513,575  7/1950  Lombard .............................. 383/84 X Primary Examiner—David H. Willse
Attorney, Agent, or Firm—Dorsey & Whitney

[57] ABSTRACT

A method of repair of direct space and indirect space inguinal hernias and a unique prosthesis enable the use of laparoscopic surgical techniques with the benefits associated therewith, while greatly reducing the recurrence of hernial defects. The prosthetic device in accordance with the present invention is a unitary piece having an abdominal wall engaging base, a hollow projection, and a slurry retaining flap. The base includes a flange that anchors the prosthetic device against the abdominal wall and a flange that covers and gives support to the surrounding abdominal wall where direct space inguinal hernia recurrence is high. The projection, situated between the ledge and the flange, is received within the defect associated with inguinal hernias and lends support thereto.

9 Claims, 4 Drawing Sheets

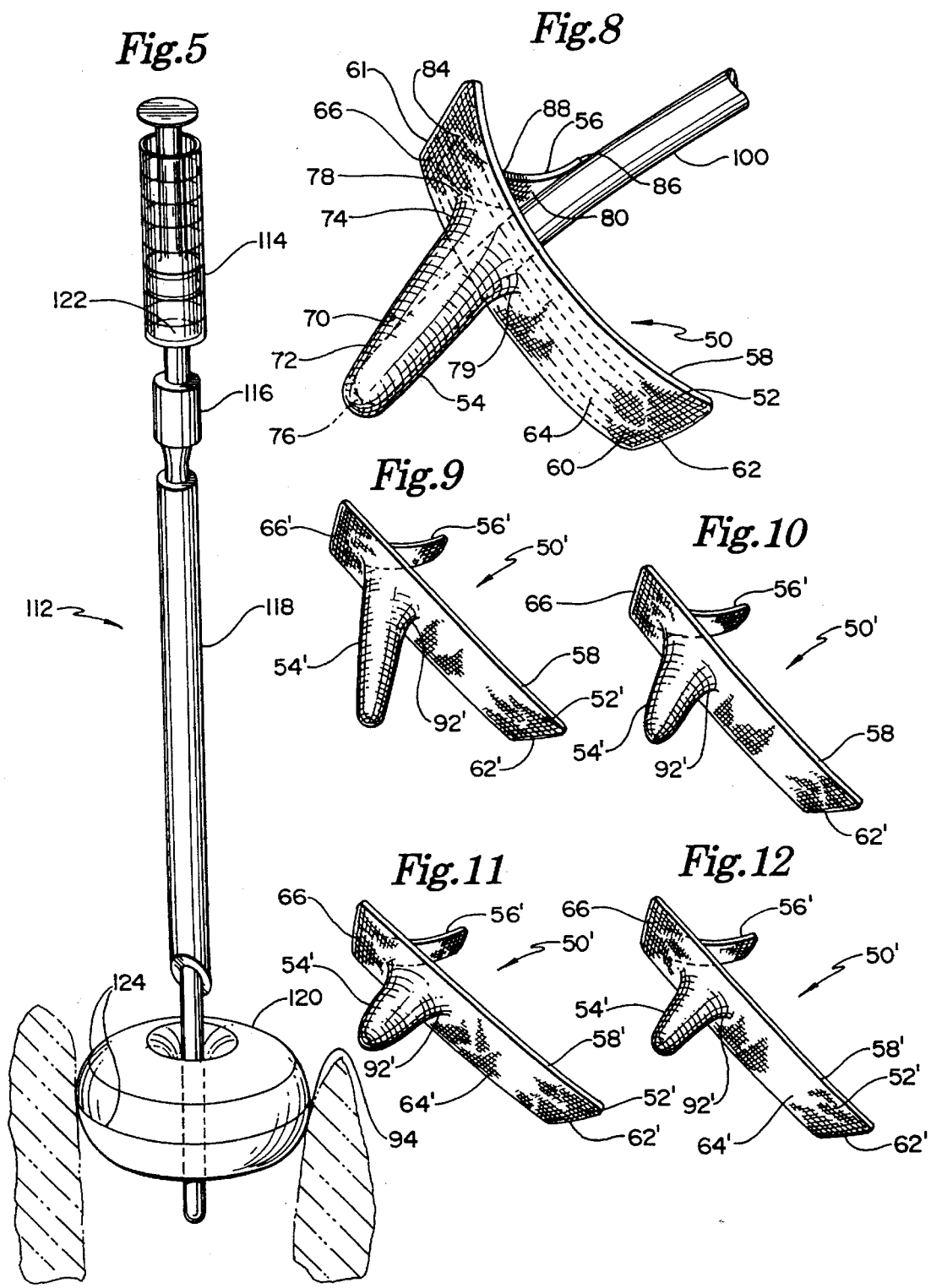

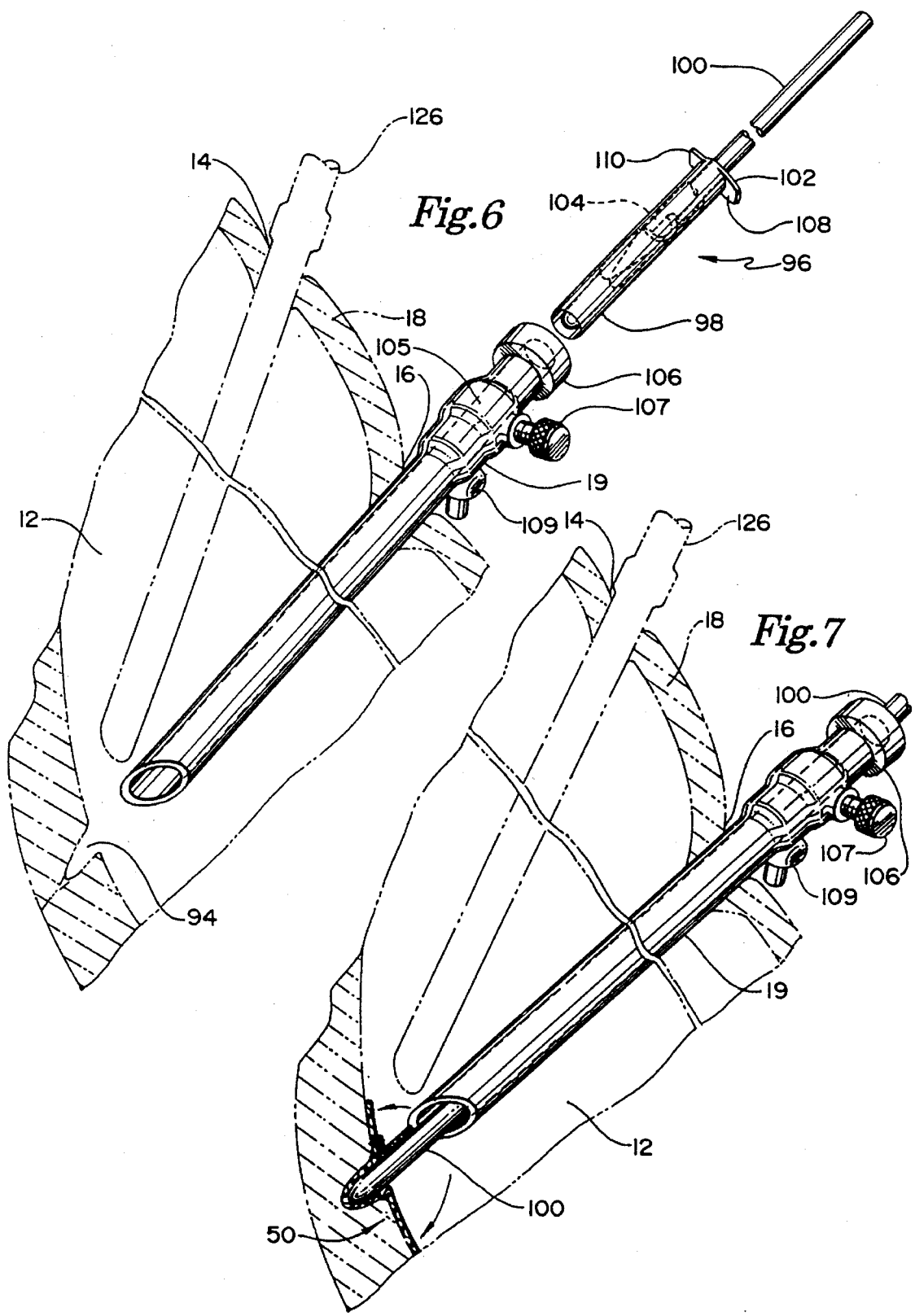

PROSTHESIS FOR REPAIR OF DIRECT SPACE AND INDIRECT SPACE INGUINAL HERNIAS

This is a continuation of application Ser. No. 07/653,083, filed Feb. 8, 1991, now abandoned.

TECHNICAL FIELD

This invention relates generally to the field of prosthetic hernioplasty, the surgical repair of inguinal hernias using a prosthesis. In particular, it relates to a method for laparoscopic prosthetic hernioplasty, that is, the laparoscopic surgical repair of direct space inguinal hernias and right and left indirect space inguinal hernias and to a unique prosthesis used during those repairs.

BACKGROUND ART

A hernia is an abnormal protrusion of an organ, tissue, or any anatomical structure through a forced opening in some part of the surrounding muscle wall. For example, if a part of the intestine were to protrude through the surrounding abdominal wall, it would create a hernia—an abdominal hernia.

Hernias occur in both males and females in the groin area, also called the inguinal region. In both sexes, the abdominal wall may be weak on both right and left sides a little above the crease in the groin. Hernias are found most frequently in males where the potential for weakness originates during the development of the fetus when the testicles are located inside the abdomen. Just prior to birth, the testicles "descend" and leave the abdomen and enter the scrotum, the sac that contains the testicles. In doing so, they push their way through the lower portion of the abdominal wall. Although the abdominal wall "closes" around the spermatic cord to which the testicle is attached after the testicles descend, the area remains slightly weakened throughout adult life. If a part of the intestines or other tissue within the abdominal cavity pushes through one of the weak spots, it forms a hernia—an inguinal hernia.

Before the piece of intestine or other abdominal cavity tissue, called the hernial mass, makes its way through the weak spot in the muscle, it must first push its way through the peritoneum, the membrane that lines the abdomen. The hernial mass does not tear the peritoneum, however. Thus, when the intestine protrudes, it merely takes the peritoneum with it and is covered by it. The peritoneal covering surrounding the piece of protruding intestine is called a hernial sac.

Inguinal hernias can be indirect space inguinal hernias or direct space inguinal hernias. An indirect space inguinal hernia occurs in the following manner. The lower part of the abdominal wall where such hernias occur, the inguinal region, is comprised of two layers, an inner layer and an outer layer. Each layer has a weak spot in it but the weak spots are not directly aligned with each other. The weak spots in each layer are positioned slightly apart from each other.

The weak spot in the inner layer is called the internal inguinal ring. In starting to form the hernia, the hernial mass begins protruding through this internal abdominal ring adjacent to the spermatic cord. To reach the weak spot in the outer layer, called the external inguinal ring, the hernial mass must move for a short distance toward the midline of the body between the internal layer and the outer layer of the abdominal wall. This passageway is called the inguinal canal. The hernia that is formed by a hernial mass that passes through the internal inguinal ring, the inguinal canal, and out through the external inguinal ring, is called an indirect space inguinal hernia.

There are two types of indirect space inguinal hernias, right and left. A hernia that is formed on the right side of the body just above the crease in the groin area is called a right indirect space inguinal hernia. In this case, the external inguinal ring is positioned medially approximately 30°–60° to the left of the internal inguinal ring. On the other hand, a hernia that is formed on the left side of the body just above the crease in the groin area is called a left indirect space inguinal hernia. In a left indirect space inguinal hernia, the external inguinal ring is positioned medially approximately 30°–60° to the right of the internal inguinal ring.

The second type of hernia is formed when the hernial mass stretches out or pushes through weakened muscle wall located proximal to the internal inguinal ring. This type of hernia is called a direct space inguinal hernia. Direct space inguinal hernias may form one or more years after a patient has had a repair of an indirect space inguinal hernia unless both areas are supported at the same time.

Traditional surgical repairs of both direct and indirect inguinal hernias have used the conventional external approach called reparative herniorrhaphy. Reparative herniorrhaphy requires laparotomy, an incision two to four inches in length made in the abdominal wall. The external approach uses a prosthetic patch that covers the outermost surface of the defect without lending any major immediate support to the defect itself or the surrounding muscle wall. Scarification of the covering and defect sufficient to allow resumption of unrestricted activities, occurs only after five to six weeks resulting in a lengthy postoperative recovery period with significant patient discomfort that requires considerable pain medication. In addition, when the external method fails to use a prosthetic device and relies solely on the patient's natural tissue for outlying support to the surrounding area, recurrence of direct space inguinal hernias is relatively high (5%). Further complications resulting from reparative herniorrahapy include infection and either a complete or partial wasting away (atrophy) of the testicles due to obstruction of the testicular blood supply.

In accordance with the method of the present invention, inguinal hernias are repaired using laparoscopic surgery. Laparoscopic surgery is less invasive, less traumatic surgery that involves visualizing the interior of the abdominal cavity using an illuminating optical instrument, a laparoscope, that is placed through a puncture orifice in the abdominal wall. Laparoscopic procedures have value as a diagnostic and operative tool for general surgery, as well as for gynecological surgery wherein such procedures are widely used. The effective use of laparoscopic procedures in the repair of inguinal hernias and the like has heretofore not been possible.

The instrument inserted into the body in a laparoscopic procedure is called a "trocar" and comprises a cannula or trocar sleeve (a hollow sheath or sleeve with a central lumen) into which fits an obturator, a solid metal rod with an extremely sharp three-cornered tip used for puncturing the muscle. The obturator is withdrawn after the instrument has been pushed into the abdominal cavity. The trocar sleeve remains in the body wall throughout the surgical procedure and various instruments used during laparoscopic procedures are introduced into the abdomen through this sleeve. Trocars are available in different sizes to accommodate various instruments.

The trocar sleeves used in laparoscopic procedures are pertinent to the present invention because they provide the pathway for insertion of the prosthetic device of the present invention into the abdomen. Representative diameters are 3, 5,10 and 11 millimeters with the 5,10 and 11 millimeters being employed most frequently in accordance with the present invention. While the use of a trocar in laparoscopic surgery is beneficial in that it results in only a small puncture wound in the patient's abdomen, the small diameter of the trocar also limits the size of surgical instruments and prosthetic devices which may be inserted in the trocar. The adaptation of laparoscopic procedures to the repair of inguinal hernias, therefore, requires the development of special surgical equipment and procedures.

The advantages of laparoscopic surgery include: simplifying the general surgery procedure so that it can be done on an outpatient basis; providing the surgeon the opportunity for viewing intra-abdominal viscera without laparotomy, a large incision made in the abdominal wall; using small puncture wounds as opposed to large incisions, lessening the trauma to anterior abdominal wall musculature; providing the surgeon with the ability to diagnose indirect inguinal hernias and direct inguinal hernias before signs and symptoms become advanced; determining incision sites for laparotomies when such incisions are appropriate; reducing both patient and insurer medical costs by shortening hospital stays; and reducing postoperative patient discomfort with recovery times measured in days as opposed to weeks.

Heretofore, indirect space inguinal hernias have been repaired by the traditional method including laparotomy of the abdominal wall and the external covering of the defect. Laparotomy is an extremely invasive procedure, requiring five to seven weeks for post-operative recovery. Moreover, preventative steps with respect to direct space inguinal hernias have not always been conventionally attempted during the repair of indirect space inguinal hernias resulting in a significant incidence of direct space inguinal hernias years after the initial occurrence. While the laparoscopic repair of inguinal hernias has been attempted using the transperitoneal approach with and without the use of prosthetic mesh, recurrence of direct space hernias remains a problem because the hernial defect has been closed with staples with no mesh used for support or a mesh patch has been used to fill the internal opening of the hernial defect without giving support to the direct space adjacent to the indirect defect.

SUMMARY OF THE INVENTION

The problems outlined above that have inhibited the effective repair of direct space and indirect space inguinal hernias are in large measure solved by the method of inguinal hernia repair and prosthetic device in accordance with the present invention. The method of repair in accordance with the present invention enables the use of laparoscopic surgical techniques in repairing inguinal hernias, with the benefits associated therewith, while greatly reducing the recurrence of hernial defects.

The prosthetic device in accordance with the present invention is generally a unitary piece having an abdominal wall engaging base, a hollow projection, and a slurry retaining flap. The base includes a flange and a ledge. The ledge anchors the prosthetic device against the abdominal wall while the flange covers and gives support to the surrounding area where direct space inguinal hernia recurrence is high. The projection, situated between the ledge and the flange, is received within the defect associated with inguinal hernias and lends support thereto.

The prosthetic device in accordance with the present invention is inserted into the abdominal cavity by means of an insertion enabling device. The insertion enabling device includes a hollow tube and an obturator. The prosthetic device is received within the hollow tube. The obturator is positioned within the projection of the prosthetic device for use in expelling the device from the hollow tube and for positioning the device in relation to the defect.

The inguinal hernia defect is sized by a sizing device that includes a syringe, a connector, a guiding catheter and a balloon tip. The syringe is filled with air or liquid which is injected into the balloon tip placed in the hernia defect. Measuring rings painted on the balloon tip allow the surgeon to extrapolate the size of the defect as the filled balloon tip expands and to select the appropriately sized prosthetic device.

Repair of an inguinal hernia in accordance with the present invention includes the steps of identifying the hernia as a direct space or an indirect space inguinal hernia; sizing the hernia defect; inserting an appropriately sized prosthetic device into the abdominal cavity; placing the prosthetic device through the internal inguinal ring; positioning the prosthetic device against the inguinal wall; and filling the projection of the prosthetic device with a slurry mixture.

One of the advantages of the present invention is that immediate support is given to the hernial defect by the projection of the prosthetic device. Moreover, direct space hernia recurrences are mitigated due to the support given to the inguinal wall by the prosthetic device. Most significantly, the present invention allows for the effective use of laparoscopic surgery in the repair of direct space and indirect space inguinal hernias, making hernial repairs safer, less painful with less morbidity for the patient and more efficient for the surgeon.

BRIEF DESCRIPTION OF THE DRAWINGS

FIG. 5 is a perspective view of a measuring instrument used to measure the size of the anatomical defect being repaired in accordance with the present invention;

FIG. 6 is a fragmentary pictorial view showing the prosthetic device in accordance with the present invention being inserted into a trocar sleeve;

FIG. 7 is a pictorial view similar to that of FIG. 6 showing the prosthesis being introduced into the defect;

FIG. 8 is a view similar to that of FIG. 3 but with an obturator extending into the projection of the prosthetic device;

FIGS. 9–12 are perspective views of prosthetic devices in accordance with the present invention with the projection depicted in various lengths and widths and extending downwardly at various angles;

DETAILED DESCRIPTION OF THE INVENTION

Figure 1:
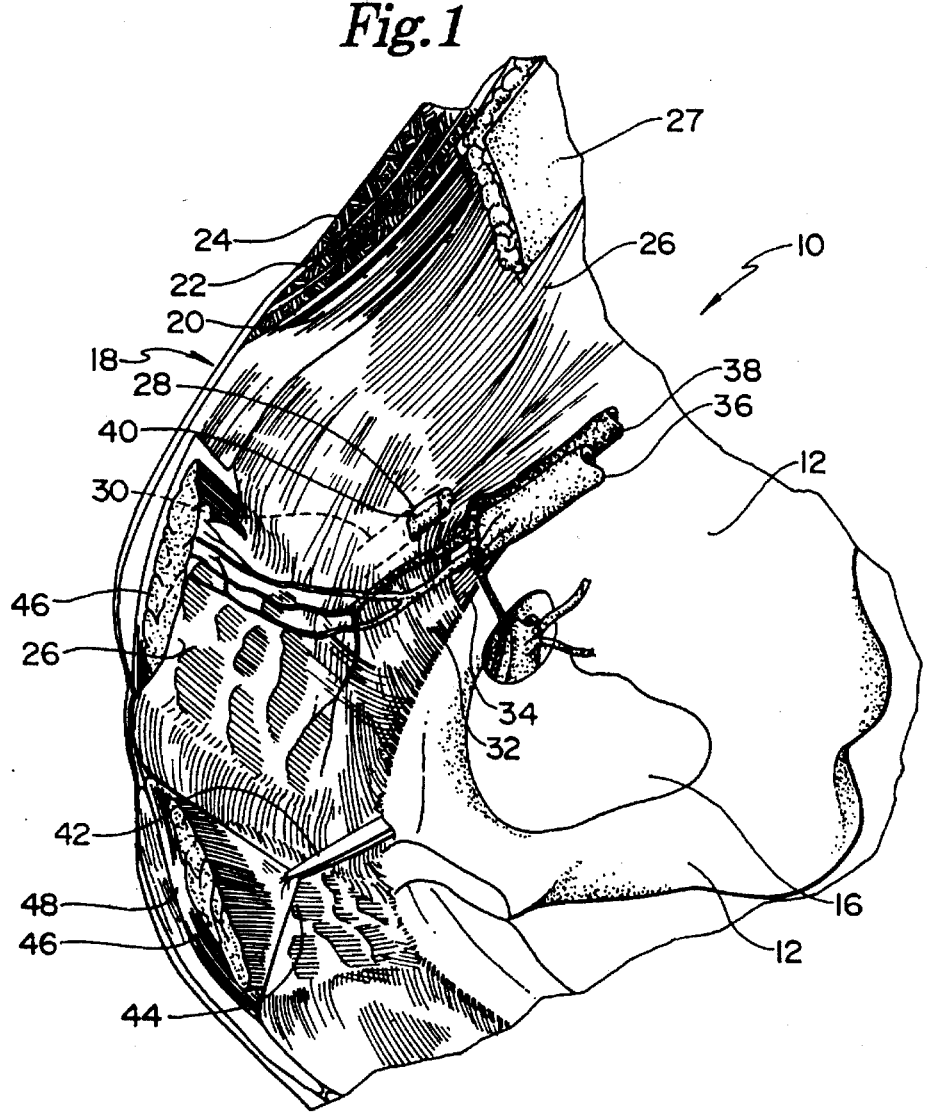
FIG. 1 is a fragmentary pictorial view of the interior of the abdomen of a patient with viscera removed.
Figure 2:
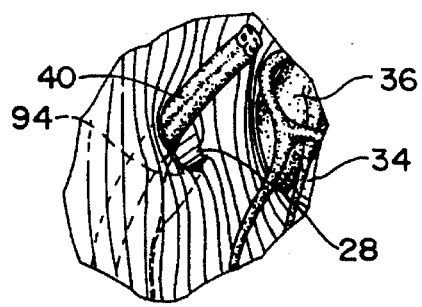
FIG. 2 is a fragmentary detail view illustrating the appearance of a typical indirect inguinal hernia defect with intrusive viscera removed.

FIG. 1 depicts the right quadrant of the lower portion of the abdominal region 10 of a patient. The lower portion of the abdominal region 10 is the region where indirect space and direct space inguinal hernias occur. The intra-abdominal cavity 12 of the patient is depicted in FIG. 1 and in enlarged detail in FIGS. 6 and 7. Puncture orifices 14, 16 are made in the abdominal wall 18 of the patient by the insertion of a trocar 19 through the abdominal wall 18 and into the intra-abdominal cavity 12. The abdominal wall 18 is comprised of three layers of muscle, the innermost transverse abdominal muscle 20, the internal oblique muscle 22 and the outermost external oblique muscle 24. The transverse abdominal muscle 20 is lined with the transversalis fascia 26, a sheet of fibrous tissue that separates the three layered abdominal wall 18 from the peritoneum 27. The peritoneum 27 abuts the transversalis fascia 26 and covers most of the viscera (not shown) located in the abdominal cavity 12.

The weak spot associated with indirect inguinal hernias is located at the internal inguinal ring 28 and the inguinal canal is indicated in FIG. 1 in phantom at 30. The weak spot associated with direct space inguinal hernia 32 is located in close proximity to the femoral ring 34. Vein 36 and iliac artery 38 extend through femoral ring 34. Spermatic cord 40 extends from the testicles (not shown) through the inguinal canal 30 to the internal inguinal ring 28. Forceps 42 are depicted in FIG. 1 as grasping rectus abdominal fascia 44 to expose muscle bundle 46 and anterior rectus sheath 48.

Indirect inguinal hernias are named by their clinical presentation. That is, an inguinal hernia occurring just above the crease in the groin area on the left side is called a left indirect inguinal hernia and an inguinal hernia occurring just above the crease in the groin area on the right side is called a right indirect inguinal hernia. As the hernial mass (not shown) moves through the inguinal canal 30, it passes through the peritoneum 27 that covers and surrounds it. The hernial mass that protrudes through the external inguinal ring is thus surrounded by the peritoneum 27 thereby creating a hernial sac (not shown).

Figure 3:
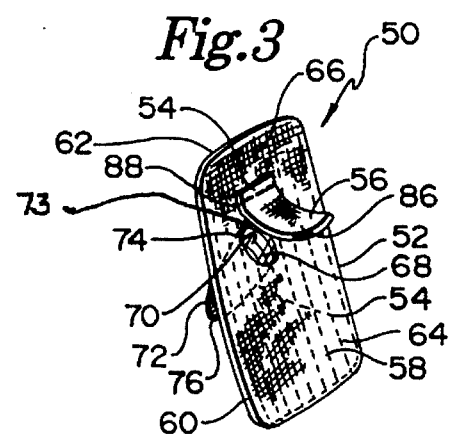
FIG. 3 is a perspective view of the preferred embodiment of the prosthetic device in accordance with the present invention.

Referring to FIGS. 3 and 8, the prosthetic device 50 for repairing direct space 32 and indirect space 28 inguinal hernias in accordance with the present invention comprises a unitary piece that broadly includes abdominal wall engaging base 52, hollow projection 54 extending outwardly from the abdominal wall engaging base 52, and slurry retaining flap 56.

Abdominal wall engaging base 52 includes upper surface 58, bottom surface 60, opposed base side margins 61, 62, flange 64, and ledge 66. The base 50 is formed of an appropriate thickness and extends from the upper surface 58 to the bottom surface 60. Ledge 66 is an appropriate length and extends from first base side margin 61 to lip edge 78 of projection 54, and anchors prosthetic device 50 against the fascia 44. Flange 64 is longer in length than ledge 66 and extends from lip edge 79 of projection 54 to the side margin 62 of base 52. Flange 64 is designed to cover the weak spot associated with direct space hernias 32.

Hollow projection 54 is positioned between flange 64 and ledge 66. Projection 54 is generally spheroconically shaped and includes a slurry receiving cavity 68, internal sidewall 70 and external sidewall 72, an uppermost portion 74 and lowermost foot 76. The internal sidewall 70 of projection 54 is continuous with the upper surface 58 of base 52. Internal sidewall 70 defines the slurry receiving cavity 68. The external sidewall 72 of projection 54 is integrally formed with the bottom surface 60 of base 52. Projection 54 extends downwardly at a generally acute angle from base 52. The diameter of the projection 54 is largest at the mouth 73 of the uppermost portion 74. Opposed lip edges 78, 79 are formed with the bottom surface 60 of base 52. Projection 54 tapers gradually from the mouth 73 to the lowermost foot 76.

Slurry retaining flap 56 includes inner face 80, outer face 82, opposed side portions 84, 86 and flap margin 88. Flap 56 is connected to upper surface 58 of base 52 at first side portion 84 by heat pressing, threading, or other suitable means. The outer face 82 of flap 56 presents a peritoneum blocking barrier to prevent peritoneum 27 from entering into the slurry receiving cavity 68 of projection 54. Inner face 80 presents a slurry retaining barrier, shown in FIG. 14, for retaining the slurry supporting mixture 90 within the cavity 68 of projection 54.

FIGS. 9–12, commonly numbered with FIGS. 3 and 8, depict differently sized embodiments of the prosthetic device in accordance with the present invention wherein the angle 92 from which projection 54 extends from base 52 varies depending on the angle that the inguinal canal 30 makes relative to the internal inguinal ring 28 in cases of indirect inguinal hernias. For instance, angle 92 may vary anywhere from 30° to 60°. It should also be noted in the alternative embodiments, FIGS. 9–12 that the length of the projection 54 may be varied as needed, depending on the length of the inguinal canal 30 into which the prosthetic device 50 is to be inserted. The width of projection 54 may also be varied depending on the diameter of defect 94.

Figure 13:
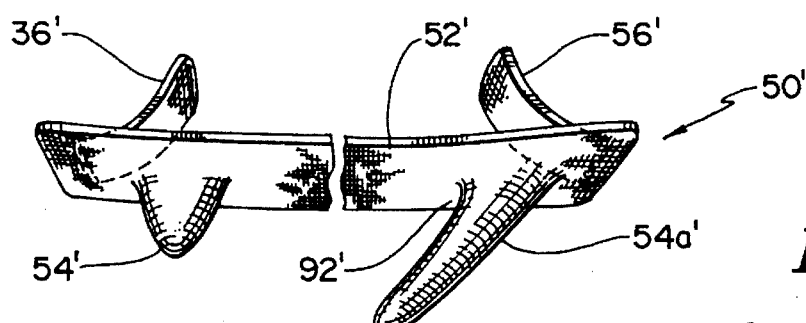
FIG. 13 is a perspective view of an alternative embodiment of a prosthetic device in accordance with the present invention especially designed for repair of a double inguinal hernia.

FIG. 13 depicts an alternative embodiment of the prosthetic device 50' in accordance with the present invention especially designed for the repair of a double inguinal hernia. A double inguinal hernia is a hernia that presents two adjacent defects, one resulting from a defect associated with the weak spot of the internal inguinal ring 28 and the other resulting from a defect associated with the weak spot of the direct space 32. It should be noted that projection 54' extends generally perpendicular from base 52' while projection 54a extends at an angle 92' from base 52'. Projections 54', 54a' may also be varied in width and length. Base 52' may be varied in length depending on the distance of the defect associated with the internal inguinal ring 28 from the defect associated with the direct space 32.

Referring to FIG. 6, the prosthetic device 50 in accordance with the present invention may be pre-packaged in a disposable plastic insertion enabling instrument 96. The pre-packaged sterile prosthetic device 50 will enable the surgeon to choose the appropriately sized prosthetic device 50 from among many such prosthetic devices 50 present in the operating room.

Referring to FIG. 6, the insertion enabling instrument 96 for use in inserting the prosthetic device 50 into a defect 94 broadly includes hollow tube 98 and disposable obturator 100. Prosthetic device 50 is depicted as received with the hollow tube 98 for insertion into the defect 94.

Hollow tube 98 broadly includes stop 102 and shank portion 104. Shank 104 has an outer diameter slightly less than the inner diameter of the central lumen 105 of instrument receiving trocar sleeve 106. Stop 102 is comprised of two opposed trocar stop flanges 108, 110. Disposable obturator 100 is positioned inside the slurry receiving cavity 68 of projection 54 for use in positioning prosthetic device 50 in inguinal canal 30 and defect 94.

Referring to FIG. 5, defect 94 may be sized by sizing device 112. Sizing device 112 broadly includes syringe 114, leur-lock connector 116, rigid guiding catheter 118, and balloon tip 120. Syringe 114 contains a balloon tip filling medium 122 comprised of liquid or air. Balloon tip 120 includes defect measuring rings 124.

Figure 4:
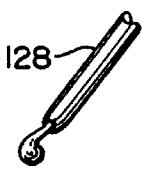
FIG. 4 is a fragmentary perspective detail view showing a hollow obturator used to inject slurry material into the hollow projection of a prosthetic device in accordance with the present invention.
Figure 15:
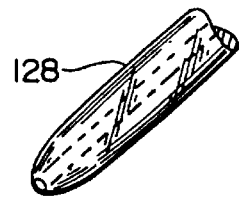
FIG. 15 is an enlarged fragmentary perspective view similar to that of FIG. 4.

Referring to FIGS. 4 and 15, a blunt tipped, hollow, slurry filling obturator 128 may be used to inject slurry supporting mixture 90 into slurry receiving cavity 68 of projection 54.

The method for repairing of direct space and indirect space inguinal hernias broadly includes the steps of inducing carbon dioxide pneumoperitoneum in the abdominal cavity 12 of the patient; inserting the trocars through the abdominal wall 18 of the patient into the abdominal cavity 12; identifying the hernia as a direct space or an indirect space inguinal hernia; inserting the sizing device 112 into the abdominal cavity 12; sizing the hernia defect; selecting an appropriately sized prosthetic device 50; using the insertion enabling instrument 96 to insert the prosthetic device 50 into the abdominal cavity 12; placing the projection of the prosthetic device 50 through the internal inguinal ring 28; positioning the prosthetic device 50 in the inguinal canal 30; positioning the prosthetic device 50 against the inguinal wall; and using the slurry filling obturator 128 to fill the prosthetic device 50 with a slurry mixture.

Referring to FIGS. 6 and 7, trocar sleeve 126, depicted in phantom lines, is introduced into abdominal cavity 12. A laparoscope (not shown) is introduced into abdominal cavity 12 through trocar sleeve 126. The laparoscope, an illuminating optical instrument, is used to visualize the interior of the abdominal cavity 12. A camera (not shown) is placed over the eyepiece of the laparoscope and the procedure is monitored on a television screen. Trocar 19 is placed midabdomen, right or left, on the same side as the hernia, and an additional trocar (not shown) is placed on the opposite side. Once the surgeon uses the sharp tipped obturator to make the puncture orifices 14, 16 in the abdominal wall 18 of the patient, the obturator is removed and the trocar sleeves 106, 126 are left in the patient. Various instruments introduced into the abdominal cavity 12 of the patient through trocar sleeve 106, may be locked into place by set screws 107, 109 thereby freeing the surgeon's hands for other tasks.

Using the laparoscope the hernia is identified as a direct, an indirect or a double hernia. A grasper (not shown) inserted through instrument receiving trocar sleeve 106 is used to grab the free inferior edge of the hernial sac (not shown). A laser fiber is then used to incise the fibroareolar or fibrous tissue of the hernial sac, and the fiber is then removed from the abdominal cavity 12.

Referring to FIGS. 5 and 6, the surgeon next introduces balloon tip 120 of defect measuring device 112 into defect 94. The balloon tip 120 of rigid guiding catheter 118 is filled with a liquid or air medium 122. Balloon tip 120 accordingly expands inside defect 94 until measuring rings 124 are flush with the diameter of defect 94. The surgeon assesses the diameter of defect 94 by extrapolation from the number of millimeters of medium 122 injected. The surgeon is then able to select the appropriate size and type of prosthetic device 50 as depicted in FIGS. 3 and 8 through 13.

Once the appropriate pre-packaged prosthetic device 50 is selected, the surgeon inserts the insertion enabling instrument 96 into central lumen 105 of instrument receiving trocar sleeve 106 by means of obturator 100. Prosthetic device 50 is pushed by obturator 100 through the hollow tube 98 of the insertion enabling instrument 96, through the central lumen 105 of instrument receiving trocar sleeve 106 and into abdominal cavity 12. Prosthetic device 50 unfurls inside abdominal cavity 12. Inside the abdominal cavity 12, the projection of the prosthetic device 50 is passed through the internal inguinal ring 28 and positioned in the inguinal canal 30. The surgeon uses obturator 100 to angle projection 54 medially, right or left as the case may be, and pushes projection 54 through inguinal canal 30 stopping short of the external inguinal ring. Base 52 rests flush against the muscle wall surrounding the internal inguinal ring 28. Flange 64 is positioned against fascia 12 of abdominal cavity 12 such that flange 64 covers the weak spot associated with direct space 32.

Figure 14:
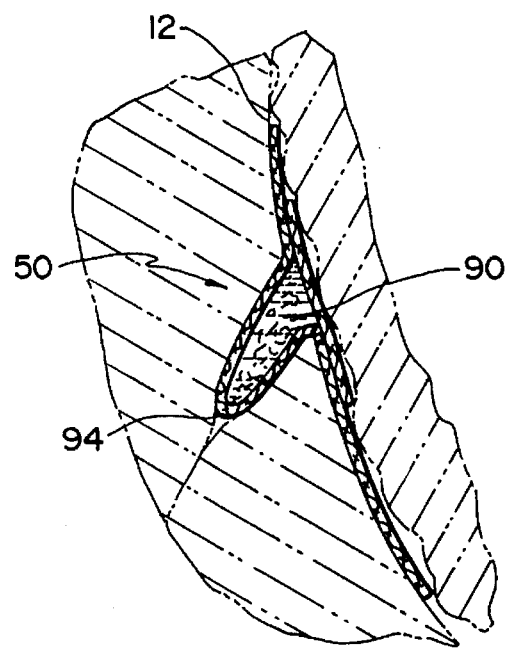
FIG. 14 is a sectional diagram showing the prosthetic device in accordance with the present invention inserted into an anatomical defect with the projection of the prosthesis substantially filled with a slurry material.

Once positioned, the slurry receiving cavity 68 of projection 54 is filled with a slurry mixture 90 of polypropylene, abdominal contents or other suitable mixtures, to lend additional support to the area and to prevent abdominal contents from entering the cavity 68. Flap 56 is then allowed to fall over and cover slurry receiving cavity 68. The laparoscopic instruments are then removed and the abdominal viscera are allowed to fall back into place, as depicted in FIG. 14.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the dependent claims rather than to the foregoing description to indicate the scope of the invention.

We claim:

1. A prosthetic device for use in laparoscopically repairing a defect in tissue, said device comprising:

a generally planar tissue engaging and reinforcing flange;

a hollow projection defining a cavity having an open end and a closed end, said projection being connected to said flange adjacent to said open end, said cavity being fillable with a fluent slurry to form a defect filling plug, said projection being sized for filling the defect; and a slurry retaining flap connected to said flange for closing said open end.

2. The prosthetic device as recited in claim 1, said flange for engaging and reinforcing tissue proximal said defect in the tissue, said projection extending at a predetermined angle away from said flange for being received in said defect.

3. The prosthetic device according to claim 2, wherein said open end is larger than said closed end, said projection tapering from said open end to said closed end.

4. The prosthetic device according to claim 3, wherein said slurry retaining flap has a free end and an end connected to said flange adjacent to said open end of the projection, whereby after said cavity is filled with fluent slurry to form the defect filling plug, the free end of the slurry retaining flap is moved whereby the flap covers the open end of the cavity.

5. A prosthetic device for use in laparoscopically repairing an inguinal hernia including a hernial defect in tissue, said device comprising:

a generally planar tissue engaging and supporting base;

a hollow projection defining a cavity having an open end and a closed end, said projection being connected to said base adjacent to said open end, extending at a predetermined angle away from said base and sized to be received in the hernial defect, said cavity being fillable with a fluent slurry to form a hernial defect filling plug; and a slurry retaining flap connected to said base for dosing said open end.

6. The prosthetic device as recited in claim 5, said base extending substantially continuously and completely around said open end and comprising a ledge for engaging tissue and a flange for supporting and reinforcing tissue proximal said hernial defect.

7. The prosthetic device according to claim 6, said open end having a generally circular perimeter, said ledge being outside and on one side of said perimeter and said flange being outside and on the opposite side of said perimeter, said slurry retaining flap being connected to said ledge and movable relative to said base.

8. The prosthetic device according to claim 7, wherein said slurry retaining flap has a free end and an end connected to said ledge adjacent to said open end of the projection, whereby after said cavity is filled with fluent slurry to form the hernial defect filling plug, the free end of the slurry retaining flap is moved whereby the flap covers the open end of the cavity.

9. The prosthetic device according to claim 8, wherein said open end is larger than said closed end, said projection tapering from said open end to said closed end.

\* \* \* \* \*